United States Patent [19]
Tsuchida et al.

[11] Patent Number: 6,008,198
[45] Date of Patent: Dec. 28, 1999

[54] PORPHYRIN METAL COMPLEX-ALBUMIN INCLUSION COMPOUND AND OXYGEN CARRIER COMPOSITION COMPRISING THE SAME

[75] Inventors: Eishun Tsuchida; Hiroyuki Nishide; Teruyuki Komatsu, all of Tokyo, Japan

[73] Assignee: Yoshitomi Pharmaceutical Industries, Ltd., Osaka, Japan

[21] Appl. No.: 08/639,798

[22] Filed: Apr. 29, 1996

[30] Foreign Application Priority Data

Apr. 28, 1995 [JP] Japan ................................. 7-106314

[51] Int. Cl.⁶ .................................................. A61K 38/00
[52] U.S. Cl. .............................. 514/21; 530/362; 530/363
[58] Field of Search .............................. 514/21; 530/362, 530/363

[56] References Cited

U.S. PATENT DOCUMENTS 5,773,417   6/1998   Bonaventura ............................ 514/21

FOREIGN PATENT DOCUMENTS

| 066884 | 12/1982 | European Pat. Off. ................. | 514/12 |
| 0 601 183 | 6/1994 | European Pat. Off. . | |
| 6-271577 | 9/1994 | Japan ...................................... | 514/12 |
| WO 96/03426 | 8/1996 | WIPO ...................................... | 514/12 |

OTHER PUBLICATIONS

Komatsu et al., "$O_2$–Transport Albumin: A New Hybrid–Haemoprotein Incorporating Tetraphenylporphinatoiron(II) Derivative" Chemistry Letters, v.9, pp. 813–814 (1995), Oct. 10, 1995.

Bonaventura et al., "Oxygen–Binding Albumins: A Novel Approach to Blood Substitutes" Artificial Cells Blood Substitutes and Immobilization Biotechnology 22(5) (1994).

Hidetoshi, Patent Abstracts of Japan 9(12) (C–261) (1984).
Kenji, Patent Abstracts of Japan 18(528) (C–1258) (1994).
Shinichi, Patent Abstracts of Japan 18(680) (C–1291) (1994).

Traylor et al., "Picket Fence Porphyrins, Synthetic Models of Oxygen Binding Hemoproteins" Journal of the American Chemical Society, vol. 101(22), 6716–6731 Oct. 24, 1979.

J.P. Collman et al., "Syntheses and NMR Characterization of Chelated Heme Model of Hemoproteins" Journal of the American Chemical Society, vol. 97, 1427–1439 (1975).

Cohen, "Binding of Porphyrin to Human Serum Albumin" Biochem. J., v. 270, pp. 325–330, 1990.

Bonaventura, CAPLUS #1996:356596 "HSA–Porphyrin Complexes" WO 96/03426, Feb. 8, 1996.

Tsuchida, JAPIO 94–271577, Sep. 27, 1994.

Mangh, "Hemoglobin; Model Systems Shed Light on Oxygen Binding" Science, vol. 187, pp. 154–156, 1975.

Eshima; J. Chem. Soc., Chem Commun., No. 3, pp. 130–132, 1985.

Tsuchida, J. Chem. Soc., Dalton Trans., pp. 1147–1151, 1984.

Chang, "Neighboring Group Effect in Heme—Limb on Monoxide Bonding" Abstract only CAPLUS #1974:345 41. 1973.

*Primary Examiner*—Johann Richter
*Assistant Examiner*—Patrick R. Delaney
*Attorney, Agent, or Firm*—Sughrue, Mion, Zinn, Macpeak & Seas, PLLC

[57] ABSTRACT

A porphyrin metal complex-albumin inclusion compound wherein a substituted porphyrin metal complex comprising, as a central, coordinated metal, a transitional metal belonging to the fourth or fifth period of the periodic law, is included in the albumin, and an oxygen carrier composition comprising said inclusion compound as an active ingredient. The compound functions as an oxygen carrier which is superior in biocompatibility, capable of adsorption and desorption of oxygen under physiological conditions, and is rather easily produced at an industrial scale.

18 Claims, No Drawings

PORPHYRIN METAL COMPLEX-ALBUMIN INCLUSION COMPOUND AND OXYGEN CARRIER COMPOSITION COMPRISING THE SAME

The present invention relates to a novel inclusion compound comprising, as an oxygen adsorption-desorption site, a porphyrin metal complex included in an albumin and to an oxygen carrier composition comprising said inclusion compound as an active ingredient.

BACKGROUND OF THE INVENTION

A porphyrin iron (II) complex present in hemoglobin and myoglobin reversibly adsorbs and desorbs oxygen molecules. An attempt to impart similar oxygen adsorption-desorption function to such natural porphyrin iron (II) complex by the use of a synthetic complex has been reported in a number of publications such as J. P. Collman, Accounts of Chemical Research, 10, 265 (1977), F. Basolo, B. M. Hoffman, and J. A. Ibers, ibid, 8, 384 (1975). For the function of a synthetic porphyrin metal complex and the like to be reproduced under the physiological conditions (in physiological salt solution, pH 7.4, at room temperature or 37° C.) and utilized in medical care (e.g., as oxygen supplying solution for artificial erythrocyte, organ preservation or oxygenator), the following requirements should be met. That is, (i) smallest possible concentration of imidazole derivatives widely used as axial base ligands for enhancing the oxygen binding capability, in view of the pharmacological action possessed by the imidazole derivatives, which sometimes causes high toxicity in vivo, and (ii) stable retention of oxygen coordinated complex by preventing the oxidation by the proton of the central metal and the oxidation via $\mu$-oxo dimer as a result of not only making the porphyrin metal complex water-soluble, but also immobilization of the same in a microscopic hydrophobic environment.

With respect to the above-mentioned requirement (i), the present inventors have already synthesized a porphyrin compound having an imidazolyl group bonded to a porphyrin ring by a covalent bond, namely, a substituted porphyrin compound having an axial base in the molecule (resulting in the molar ratio of porphyrin/imidazole suppressed to the minimum necessary ratio of 1:1), and clarified that this compound forms a stable oxygen coordinated complex (Japanese Patent Unexamined Publication No. 271577/1994). When the axial base is bonded by an ester bond in this porphyrin complex, the compound exhibits high biodegradability, making itself highly advantageous for administration to living organisms. In other words, the development of a highly safe oxygen binding site (porphyrin metal complex) has been completed by the present inventors.

On the other hand, it is known that the above-mentioned requirement (ii) regarding the provision of microscopic hydrophobic environment to the porphyrin metal complex can be met by utilizing a micelle containing a surfactant, or an endoplasmic reticulum having two molecular membranes of phospholipid. However, micelles are morphologically dynamic, inferior in stability as compared to endoplasmic reticulum having two molecular membranes, and are capable of forming only poorly hydrophobic environments. Therefore, endoplasmic reticulum having two molecular membranes is frequently used as a carrier, which has a relatively stable shape and is capable of providing sufficiently hydrophobic environments, so as to provide a hydrophobic environment to the complex. Thus, an oxygen carrier composition has been developed, which carries oxygen stably under physiological conditions as a result of dispersion, with high orientation, of porphyrin metal complex between the two molecular membranes of phospholipid endoplasmic reticulum.

Noting the probability of inclusion, with high orientation, of porphyrin metal complex in the hydrophobic environment of phospholipid having two molecular membranes, as achieved by the introduction of an alkyl substituent having hydrophilic ends onto the porphyrin ring, thereby to make an emphilic structure of the porphyrin, the present inventors synthesized various emphilic porphyrin metal complexes and include-oriented them in phospholipids having two molecular membranes, whereby a series of oxygen carrier compositions effective in aqueous phase systems have been developed (Japanese Patent Unexamined Publication Nos. 101490/1985 and 213777/1983).

However, the use of a large amount of phospholipid to prepare such oxygen carrier composition leaves room for an improvement in terms of industrial scale production and biocompatibility inclusive of metabolism.

It is therefore an object of the present invention to provide a novel compound comprising, as an oxygen absorption-desorption site, a porphyrin metal complex, which is superior in biocompatibility and permits rather easy production at an industrial scale, and an oxygen carrier composition comprising the same.

The present inventors have investigated the molecular design of an oxygen carrier capable of stably carrying oxygen under physiological conditions, expression of the function thereof and high biocompatibility of a carrier capable of providing a hydrophobic environment to the porphyrin metal complex, and found that albumin which occupies 50–55% of plasma protein and which carries various compounds in the living body can provide a superior hydrophobic environment to the porphyrin metal complex, and that a porphyrin metal complex-albumin inclusion compound obtained by including a certain porphyrin metal complex in the albumin forms a stable oxygen coordinated complex in water, and thus is able to function as an oxygen carrier.

Accordingly, the present invention provides a porphyrin metal complex-albumin inclusion compound wherein a substituted porphyrin metal complex having, as a central coordinated metal, a transition metal belonging to the fourth or fifth period of the periodic law, included in albumin.

The substituted porphyrin metal complex is most preferably a 5,10,15,20-tetra[$\alpha,\alpha,\alpha,\alpha$-o-(substituted amide)phenyl]porphyrin metal complex having the following formula (I):

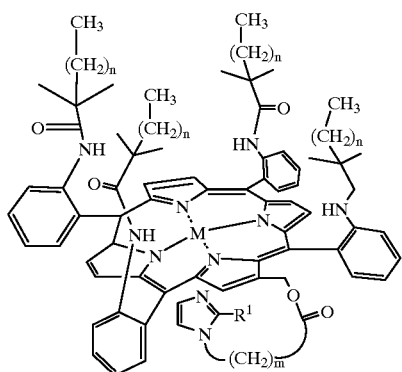

wherein $R^1$ is a hydrogen or a methyl, M is an iron or cobalt ion, n is an integer of from 0 to 17 and m is an integer of from 3 to 17, or a porphyrin metal complex of the formula (II)

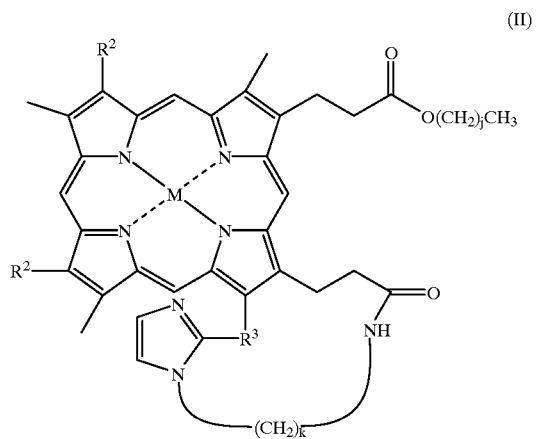

wherein the two $R^2$ groups are the same or different and each is a vinyl or a 1-alkyloxyethyl group of the formula: —$(CH_3)CHO(CH_2)_hCH_3$ wherein h is an integer of from 0 to 17, $R^3$ is a hydrogen or a methyl, M is an iron or cobalt ion, j is an integer of from 0 to 17 and k is an integer of from 3 to 10.

The porphyrin metal complex of the formula (I) or (II) which is an oxygen carrier comprises iron or cobalt as the central divalent metal M.

The origin of the albumin is not particularly limited, but it is preferably human serum albumin or recombinant human serum albumin. In particular, the recent progress in gene recombination has enabled the provision of a highly pure recombinant human serum albumin having the completely same structure, composition and physicochemical characteristics with human serum albumin [see Yokoyama and Ohmura, Clinical Molecular Medicine, 1, 939 (1993)], and a porphyrin metal complex-recombinant human serum albumin inclusion compound wherein a substituted porphyrin metal complex has been included in the recombinant human serum albumin can be entirely prepared by synthesis, thus making industrial production easier.

In another aspect of the present invention, an oxygen carrier composition comprising, as an active ingredient, the above-mentioned porphyrin metal complex-albumin inclusion compound is provided.

The present invention is explained in more detail in the following.

In the present invention, the albumin including the porphyrin metal complex to be detailedly described later is a simple protein with its main function being control of colloidal osmotic pressure in blood, and also functions as a carrier protein of nutritive substances, metabolites thereof, drugs and the like. The present invention relies on such nonspecific binding capacity of albumin, which is absent in other proteins.

In addition, albumin is markedly advantageous in the application to the living body, particularly as an erythrocyte substitute, as compared to the system using phospholipid endoplasmic reticulum, since it is a blood plasma protein.

The origin of the albumin to be used in the present invention is not particularly limited and the albumin is exemplified by human serum albumin, recombinant human serum albumin and bovine serum albumin. In consideration of the application to humans, however, the use of human serum albumin or recombinant human serum albumin is desirable.

The substituted porphyrin metal complex to be included in albumin in the present invention is not subject to any particular limitation as long as it is a substituted porphyrin metal complex having, as a central coordinated metal, a transition metal (e.g., chromium, manganese, iron, cobalt and ruthenium) belonging to the fourth or fifth period of the periodic law. The central coordinated metal is preferably iron or cobalt, and particularly preferably iron. An imidazole-bound substituted porphyrin metal complex is particularly preferable.

In the preferred embodiment of the present invention, the substituted porphyrin metal complex is expressed by the above-mentioned formula (I) or (II).

5,10,15,20-tetrakis(o-pivalamidophenyl)porphyrinato copper (II) was prepared according to Collman et al., *J. Am. Chem. Soc.*, 1975, 97, 1427.

Phosphorus oxychloride (3.5 ml, 37.3 mmol) was dropped into N,N-dimethylformamide (DMF) (3.5 ml) in an ice-water bath and the mixture was stirred for 1 hour at room temperature, giving a Vilsmeier reagent. To the porphyrin (0.2 g, 0.19 mmol) solution dissolved in dry $CH_2Cl_2$ (40 ml) was added dropwise at 25° C. and refluxed for 15 hours, yielding a green solution. Saturated aqueous sodium acetate (50 ml) was added to the mixture at 25° C. and further stirred for 3 hours at 40° C. The mixture was extracted by $CHCl_3$ and washed with water. After drying ($Na_2SO_4$), the organic layer was chromatographed on a silica gel flash column using $CHCl_3$-ethylacetate (6/1 v/v) as the eluent. The residue was dried at room temperature in vacuo to give a purple product, (2-formyl-5,10,15,20-tetrakis(o-pivalamidophenyl) porphyrinato copper (II), 0.16 g, 78%).

To a $CH_2Cl_2$ solution (20 ml) of (2-formyl-5,10,15,20-tetrakis(o-pivalamidophenyl)porphyrinato copper (II) (0.16 g), conc. $H_2SO_4$ (20 ml) was added and vigorously stirred for 10 min. The resulting green solution was dropwise to $CH_2Cl_2$-ice-water (1/3 v/v) (800 ml) and neutralized by $NaHCO_3$ slowly. The mixture was extracted by $CHCl_3$ and washed with water. After drying ($Na_2SO_4$), the organic layer was chromatographed on a silica gel flash column using $CHCl_3$-ethylacetate (4/1 v/v) as the eluent. The residue was dried at room temperature in vacuo to give a purple product, (2-formyl-5,10,15,20-tetrakis(o-pivalamidophenyl) porphyrin, 0.12 g, 85%).

$NaBH_4$ (41.5 mg, 1.1 mmol) was added to a solution of $CH_2Cl_2$—MeOH (1/3 v/v) (8 ml) containing 2-formyl-5,10, 15,20-tetrakis(o-pivalamidophenyl)porphyrin (0.11 g, 0.11 mmol) under argon stirred for 15 min. After adding water to the solution, the mixture was extracted by $CHCl_3$ and washed with water. After drying (Na$_2$SO$_4$), the organic layer was chromatographed on a silica gel flash column using CHCl$_3$—MeOH (10/1 v/v) as the eluent. The residue was dried at room temperature in vacuo to give a purple product, (2-hydroxymethyl-5,10,15,20-tetrakis(o-pivalamidophenyl) porphyrin, 0.11 g, 94%).

8-Imidazol-1-yloctanoic acid hydrochloride (90.1 mg, 0.37 mmol) and triethylamine (TEA, 0.1 ml, 0.74 mmol) were dissolved in dry DMF (4 ml) and stirred for 10 min. After removing TEA under reduced pressure, 2-hydroxymethyl-5,10,15,20-tetrakis(o-pivalamidophenyl) porphyrin, 76 mg, 73 μmol), 4-(N,N-dimethylamino) pyridine (DMAP, 4.5 mg, 37 μmol) and dicyclohexylcarbodiimide (DCC, 75.4 mg, 0.37 mmol) were added to the solution and stirred for 84 hours at room temperature in darkness. The mixture was chromatographed on a silica gel flash column using CHCl$_3$—MeOH (30/1 v/v) as the eluent. The residue was dried at room temperature in vacuo to give a purple product, 2-(8-imidazol-1-yloctanoyloxymethyl)-5, 10,15,20-tetrakis(o-pivalamidophenyl)porphyrin (80 mg, 89%).

A dry tetrahydrofuran (THF, 50 ml) solution of 2-(8-imidazol-1-yloctanoyloxymethyl)-5,10,15,20-tetrakis(o-pivalamidophenyl)porphyrin (80 mg, 64 μmol) was added dropwise to anhydrous iron (II) bromide (0.86 g, 4 mmol) under dry argon and the mixture was refluxed under argon for 4 hours. The mixture was extracted by CHCl$_3$ and washed with water. After drying (Na$_2$SO$_4$), the organic layer was chromatographed on a silica gel flash column using CHCl$_3$—MeOH (4/1 v/v) as the eluent. The residue was dried at room temperature in vacuo to give a purple products, 2-(8-imidazol-1-yloctanoyloxymethyl)-5,10,15, 20-tetrakis(o-pivalamidophenyl)porphyrinato iron (II) (100 mg, 84%).

The 5,10,15,20-tetra[α,α,α,α-o-(substituted amide) phenyl]porphyrin metal complex of the formula (I) importantly comprises an alkyl imidazolyl group bonded to the 2-position of a porphyrin ring. The present inventors have found that the porphyrin complex without such imidazolyl group in the molecule immediately degrades without forming a stable oxygen complex in an aqueous phase system, despite the addition of an excess external imidazole derivative (e.g., 1-methylimidazole).

The porphyrin of the formula (II) is a protoporphyrin IX derivative similar to hemoglobin in the living body, and is superior in biocompatibility. Of the compounds of the formula (II), a porphyrin derivative wherein R$^2$ is vinyl can be synthesized by the method of T. G. Traylor et al., J. Am. Chem. Soc., 101, 6716 (1979). A porphyrin derivative wherein R$^2$ is 1-alkyloxyethyl can be synthesized by, for example, the following process.

That is, 8,13-bis(1'-alkyloxyethyl)-3,7,12,17-tetramethyl-2,18-bis(2'-alkyloxycarbonylethyl)-21H,23H-porphyrin synthesized by the method described in Tsuchida et al., Chem. Lett., 1953, (1994) is dissolved in 1–5N hydrochloric acid, and the mixture is stirred for 1–24 hours at room temperature. When the porphyrin is insoluble in hydrochloric acid, an organic solvent such as tetrahydrofuran and acetone is added as necessary to homogeneously dissolve the porphyrin. After the completion of the reaction, the solvent is distilled away under reduced pressure, and the residue is extracted with chloroform, dichloromethane, benzene and the like, which is followed by washing with pure water. Then, the organic layer is evaporated to dryness and subjected to separation and purification by silica gel column chromatography to give a monoester compound wherein one of the ester bonds has been hydrolyzed. This monoester compound is dissolved in anhydrous tetrahydrofuran, dimethylformamide and the like containing a base such as triethylamine, pyridine, 4-dimethylaminopyridine and the like under a nitrogen atmosphere. Chloride pivalate is added at −20–30° C., preferably −20–0° C., and the mixture is stirred for 10–60 minutes. 1-(3-Aminoalkyl)imidazole is dropwise added and the mixture is reacted at −20–30° C. for 1–24 hours. The solvent is removed under reduced pressure, and the residue is extracted with an organic solvent such as chloroform, dichloromethane and benzene, which is followed by washing with pure water. Then, the organic layer is evaporated to dryness under reduced pressure and subjected to separation and purification by silica gel column chromatography to give the desired 8,13-bis(1'-alkyloxyethyl)-2-(2'-alkyloxycarbonylethyl-18-(2'-(3''-imidazolyl)alkyl)aminocarbonylethyl)-3,7,12,17-tetramethyl-21H,23H-porphyrin.

The introduction of the central metal, namely, the introduction into iron complex, cobalt complex and the like, is carried out by a conventional method [e.g., D. Dolphin ed., The porphyrin, Academic Press (1978)]. In general, a porphyrinato iron (III) complex is obtained from an iron complex and a porphyrinato cobalt (II) complex is obtained from a cobalt complex.

The substituted porphyrin metal complex-albumin inclusion compound of the present invention is prepared by the following step. That is, a porphyrin metal [e.g., 2-(8'-(N-imidazolyl)octanoyloxymethyl) -meso-tetra(α,α,α,α-o-pivalamidophenyl)porphyrinato iron (III) complex] is dissolved in a water-soluble solvent (e.g., dimethylformamide, dimethylsulfoxide and methanol) and an aqueous solution of albumin (e.g., human serum albumin) in, for example, water, ethanol, phosphate buffer (pH 5–9), physiological saline or Krebs-Ringer solution is added, followed by gentle shaking. The obtained aqueous dispersion is concentrated by ultrafiltration using, for example, an ultrafiltration membrane having a cut off molecular weight of 20,000–40,000, to about 10% of the total amount. Water is added and the ultrafiltration is repeated to give a porphyrin metal complex-albumin inclusion compound. This dispersion is free of sedimentation or coagulation even after preservation at 4–35° C. for several months, and is stable.

When the central metal of the porphyrin metal complex is iron (III), an oxygen-binding activity can be imparted thereto by a conventional method such as addition of a reducing agent (e.g., aqueous solution of sodium dithionite or ascorbic acid) under a nitrogen atmosphere to reduce the central metal iron from trivalent to divalent.

Such reduction can be carried out by the addition of not only a reducing agent but also a palladium-carbon/hydrogen gas. For example, a porphyrin iron (III) complex is dissolved in dry dichloromethane, benzene, toluene and the like; a small amount of palladium-carbon is added; and a hydrogen gas is sufficiently blown in at room temperature, whereby the central metal iron is reduced. After the reduction, the palladium-carbon is filtered off and the filtrate is dried in vacuo to give a porphyrin iron (II) compound.

The above-mentioned reduction can be carried out before inclusion reaction.

The porphyrin metal complex-albumin inclusion compound of the present invention thus obtained comprises a porphyrin metal complex included and immobilized in the inner hydrophobic region formed by albumin. The number of the porphyrin metal complex included and bonded to one mole of albumin can be determined by forming a Scatchard plot [C. J. Halfman, T. Nishida, Biochemistry, 11, 3493 (1972)]. For example, the number of bonding of a substituted porphyrin metal complex (e.g., 2-(8'-(2"-methyl-1-imidazolyl))octanoyloxymethyl -meso-tetra($\alpha,\alpha,\alpha,\alpha$-o-pivalamidophenyl)porphyrinato iron (II) complex) to the albumin (e.g., human serum albumin) is 1–3.

As has been stated, the oxidation by the proton of the central metal and oxidative degradation via $\mu$-oxo dimer can be completely inhibited by the oxygen adsorption site (porphyrin metal complex) which has been immobilized in the inner hydrophobic environment of albumin. Consequently, the inclusion compound of the present invention can retain the stable oxygen coordinated complex in an aqueous phase system.

The porphyrin metal complex-albumin inclusion compound of the present invention comprises a synthetic substituted porphyrin metal complex as the oxygen binding site. Hence, its affinity for oxygen, toxicity, biodegradability and the like can be optionally controlled by varying the chemical structure of the substituted porphyrin metal complex. It has been clarified by the present invention that, while the inclusion in albumin requires a certain balance between hydrophilicity and hydrophobicity (polarity) and certain molecular volume of the porphyrin metal complex, a bulky molecule can be included and sufficiently exert the desired function, such as tetraphenylporphyrin derivative of the formula (I) having a molecular volume of 10–21 nm$^3$ which is about 2–10 times greater than the molecular volume of 2–3.5 nm$^3$ of protoporphyrin of the formula (II). This finding is expected to offer a new aspect of the molecular design of the albumin complex.

As is evident from the foregoing explanation, the porphyrin metal complex-albumin inclusion compound of the present invention quickly forms a stable oxygen coordinated complex upon contact with oxygen. This oxygen coordinated complex is capable of adsorbing or desorbing oxygen according to the oxygen partial pressure. Such oxygen adsorption and desorption can be stably repeated reversibly according to the oxygen partial pressure. The oxygen bond dissociation is completed quickly, and the inclusion compound of the present invention can function as a semi-artificial oxygen carrier or entirely synthesized oxygen carrier when human serum albumin is used, which is capable of carrying oxygen in the blood streams in the living body.

According to the experiment done by the present inventors, the half-life ($\tau_{1/2}$) of the oxygen coordinated complex in a porphyrin iron (II) complex-albumin inclusion compound [e.g., 2-(8'-(2"-methyl-1-imidazolyl))octanoyloxymethyl-meso-tetra($\alpha,\alpha,\alpha,\alpha$-o-pivalamidophenyl)porphyrinato iron (II) complex-human serum albumin inclusion compound] at 25° C. was not less than 16 hours. In contrast, that of the oxygen coordinated complex included between the two molecular layers of phospholipid endoplasmic reticulum under the same conditions was not less than 4 hours, and that in a micelle solution in which dispersion was effected by the use of surfactant Triton X-100 (trademark) was short and not more than one minute. Thus, the life time of an oxygen coordinated complex can be greatly prolonged by the inclusion of the porphyrin metal complex in the inner hydrophobic environment of albumin.

The inclusion of the substituted porphyrin metal complex in an inner hydrophobic environment of albumin has led to the superior function of the porphyrin metal complex-albumin inclusion compound of the present invention as an oxygen carrier, as mentioned above. When the central metal is a transition metal belonging to the fourth or fifth period of the periodic law, moreover, the compound of the present invention can act as a catalyst in a wide range of reactions such as oxidative reduction, oxidative oxidation, active oxygen decomposition, optical activation of oxygen and oxygenation. In other words, the inclusion compound of the present invention is useful per se as a synthesized oxygen carrier, as well as a gas adsorbent, an oxygen adsorbent and desorbent, and a catalyst in oxidative oxidation or reduction, oxygenation and optical activation of oxygen. The inclusion compound of the present invention is easy to produce and suitable for industrial production when a recombinant human serum albumin is used.

The present invention is explained in the following by illustrative Examples to which the invention is not limited.

EXAMPLE 1

According to the method described in Japanese Patent Unexamined Publication No. 271577/1994, 2-(8'-(2"-methyl-1"-imidazolyl)octanoyloxymethyl)-5,10,15,20-tetrakis($\alpha,\alpha,\alpha,\alpha$-o-pivalamidophenyl)porphyrinato iron (III) complex was obtained. To a solution of 0.14 mmol of this complex in dimethyl sulfoxide (12 ml) was added an aqueous solution of human serum albumin (0.1 mmol) in phosphate buffer (100 ml, pH 7.4, 1/30 mM), and the mixture was shaken. The mixture was concentrated to 20 ml by ultrafiltration (ultrafilter manufactured by ADVANTEC; cut off molecular weight 20,000). An aqueous solution of phosphate buffer (92 ml, pH 7.4, 1/30 mM) was added and the mixture was shaken, which was followed by concentration by ultrafiltration and dilution with an aqueous solution of phosphate buffer, whereby the desired dispersion of porphyrin iron (III) complex-albumin inclusion compound was obtained. This dispersion was preserved at room temperature or 4° C. for several months. As a result, no sedimentation or coagulation was found, and the dispersion was stable.

A small amount of an aqueous solution of sodium dithionite was added to this dispersion under nitrogen atmosphere to reduce the central metal iron of the porphyrin complex to a divalent iron, whereby the objective dispersion of 2-(8'-(2"-methyl-1"-imidazolyl)octanoyloxymethyl)-5,10,15,20-tetrakis ($\alpha,\alpha,\alpha,\alpha$-o-pivalamidophenyl)porphyrinato iron (II) complex-albumin inclusion compound was obtained.

A carbon monoxide gas was passed through this dispersion, and the light (500 W) was irradiated in an ice bath with nitrogen gas aeration to give a deoxy type complex. This dispersion was diluted 1/50-fold and transferred into a quartz spectrometry cell, and the cell was sealed under a nitrogen atmosphere. The visible absorption spectra thereof were $\lambda_{max}$: 563 nm, 542 nm, 439 nm, which correspond to the spectrum of a penta-coordinated deoxy type complex having one intramolecular base.

The spectrum immediately changed when an oxygen gas was passed through this dispersion, giving spectra of $\lambda_{max}$: 548 nm, 424 nm, which apparently suggests that the porphyrin iron (II) complex included in albumin had changed to an oxygenated complex. A nitrogen gas was passed through the dispersion of this oxygenated complex, as a result of which the visible absorption spectrum changed from the oxygen type spectrum to the deoxy type spectrum, thus confirming the reversible adsorption and desorption of oxygen. Repeats of alternative aeration of oxygen and nitrogen enabled repetitive adsorption and desorption of oxygen. The half life time of the above-mentioned oxygenated complex was not less than 16 hours at 25° C.

EXAMPLE 2

In the same manner as in Example 1 except that 2-(18'-(N-imidazolyl)octadecanoyloxymethyl)-5,10,15,20-tetrakis (α,α,α,α-o-(2,2-dimethyloctadecanamidophenyl) porphyrinato iron (III) complex (1.4 mmol) was used instead of the porphyrin iron (III) complex used in Example 1 and bovine serum albumin was used instead of human serum albumin, a dispersion of 2-(18'-(N-imidazolyl) octadecanoyloxymethyl)-5,10,15,20-tetrakis(α,α,α,α-o-(2, 2-dimethyloctadecanamidophenyl)porphyrinato iron (II) complex-albumin inclusion compound was prepared. The visible absorption spectra were $\lambda_{max}$: 562 nm, 541 nm, 436 nm, which correspond to the spectrum of a deoxy type complex. The aeration of oxygen gas in the same manner as in Example 1 provided visible absorption spectra ($\lambda_{max}$ 544 nm, 423 nm) corresponding to the spectrum of an oxygenated complex. A nitrogen gas was passed through the dispersion of this oxygenated complex, whereby the original deoxy type spectrum was obtained, thus confirming the reversible adsorption and desorption of oxygen. The half life time of the above-mentioned oxygenated complex was not less than 15 hours at 25° C.

EXAMPLE 3

2-(8'-(N-Imidazolyl)octanoyloxymethyl)-5,10,15,20-tetrakis-(α,α,α,α-o-pivalamidophenyl)porphyrinato iron (III) complex (1.4 mmol) was dissolved in benzene (20 ml), and a small amount of 10% palladium black was added. A hydrogen gas was blown in for 20 minutes to reduce the central metal iron, and the catalyst was filtered off. A carbon monoxide gas was passed through this solution to convert the porphyrin iron complex to a carbon monoxide complex, and the solvent was distilled away under reduced pressure. The solid residue was dissolved in dimethyl sulfoxide solution (10 ml) with aeration of carbon monoxide gas, and human serum albumin in phosphate buffer (100 ml, pH 7.4, 1/30 mM) was added, which was followed by shaking. The mixture was concentrated to 20 ml by ultrafiltration (ultrafilter manufactured by ADVANTEC; cut off molecular weight 20,000). An aqueous solution of phosphate buffer (92 ml, pH 7.4, 1/30 mM) was added and the mixture was shaken, which was followed by concentration by ultrafiltration and dilution with an aqueous solution of phosphate buffer, whereby the desired dispersion of carbon monoxide-coordinated porphyrin iron (II) complex-albumin inclusion compound was obtained.

Irradiation of light (500 W) in an ice bath with nitrogen gas aeration gave a deoxy compound, whereby the objective dispersion of 2-(8'-(N-imidazolyl)octanoyloxymethyl)-5,10, 15,20-tetrakis-(α,α,α,α-o-pivalamidophenyl)porphyrinato iron (II) complex-albumin inclusion compound was obtained.

This dispersion was diluted 1/50-fold and transferred into a quartz spectrometry cell, and the cell was sealed under a nitrogen atmosphere. The visible absorption spectra thereof were $\lambda_{max}$: 564 nm, 541 nm, 435 nm, which correspond to the spectrum of a penta-coordinated deoxy type complex having one intramolecular base.

The spectrum immediately changed when an oxygen gas was passed through this dispersion, giving spectra of $\lambda_{max}$: 546 nm, 423 nm, which apparently suggests that the porphyrin iron (II) complex included in albumin had changed to an oxygenated complex. A nitrogen gas was passed through the dispersion of this oxygenated complex, as a result of which the visible absorption spectrum changed from the oxygen type spectrum to the deoxy type spectrum, thus confirming the reversible adsorption and desorption of oxygen. Repeats of alternative aeration of oxygen and nitrogen enabled repetitive adsorption and desorption of oxygen. The half life time of the above-mentioned oxygenated complex was not less than 14 hours at 25° C.

EXAMPLE 4

In the same manner as in Example 1 except that a recombinant human serum albumin (manufactured by The Green Cross Corporation) was used instead of human serum albumin, a dispersion of 2-(8'-(2"-methyl-1"-imidazolyl) octanoyloxymethyl)-5,10,15,20-tetrakis(α,α,α,α-o-pivalamidophenyl)porphyrinato iron (III) complex-recombinant human serum albumin inclusion compound was prepared. The visible absorption spectra were $\lambda_{max}$: 562 nm, 540 nm, 439 nm, which correspond to the spectrum of a deoxy type complex. The aeration of oxygen gas in the same manner as in Example 1 provided visible absorption spectra ($\lambda_{max}$: 545 nm, 423 nm) corresponding to the spectrum of an oxygenated complex. A nitrogen gas was passed through the dispersion of this oxygenated complex, whereby the original deoxy type spectrum was obtained, thus confirming the reversible adsorption and desorption of oxygen. The half life time of the above-mentioned oxygenated complex was not less than 14 hours at 25° C.

EXAMPLE 5

2-(8'-(N-Imidazolyl)octanoyloxymethyl)-5,10,15,20-tetrakis-(α,α,α,α-o-(2,2-dimethylhexanamido)phenyl) porphyrinato cobalt (II) complex (0.14 mmol) was dissolved in dimethyl sulfoxide (12 ml), and human serum albumin (0.1 mmol) in phosphate buffer (100 ml, pH 7.4, 1/30 mM) was added, which was followed by shaking. The mixture was concentrated to 20 ml by ultrafiltration (ultrafilter manufactured by ADVANTEC; cut off molecular weight 20,000). An aqueous solution of phosphate buffer (92 ml, pH 7.4, 1/30 mM) was added and the mixture was shaken, which was followed by concentration by ultrafiltration and dilution with an aqueous solution of phosphate buffer, whereby the desired dispersion of porphyrin cobalt (II) complex-albumin inclusion compound was obtained. This dispersion was preserved at room temperature or 4° C. for several months. As a result, no sedimentation or coagulation was found, and the dispersion was stable. The porphyrin cobalt (II) complex was converted to a deoxy type complex by the aeration of nitrogen gas. This dispersion was diluted 1/50-fold and transferred into a quartz spectrometry cell, and the cell was sealed under a nitrogen atmosphere. The visible absorption spectra thereof were $\lambda_{max}$: 530 nm, 411 nm, which correspond to the spectrum of a penta-coordinated deoxy type complex having one intramolecular base.

The spectrum immediately changed when an oxygen gas was passed through this dispersion, giving spectra of $\lambda_{max}$: 547 nm, 416 nm, which apparently suggests that the porphyrin cobalt (II) complex included in albumin had changed to an oxygenated complex. A nitrogen gas was passed through the dispersion of this oxygenated complex, as a result of which the visible absorption spectrum changed from the oxygen type spectrum to the deoxy type spectrum, thus confirming the reversible adsorption and desorption of oxygen. Repeats of alternative aeration of oxygen and nitrogen enabled repetitive adsorption and desorption of oxygen. The half life time of the above-mentioned oxygenated complex was not less than 11 hours at 25° C.

EXAMPLE 6

8,13-bis(1'-Methoxyethyl)-3,7,12,17-tetramethyl-2,18-bis(2'-methyloxycarbonylethyl)-21H,23H-porphyrin (0.34 mg, 0.52 mmol) synthesized by the method described in Tsuchida et al., Chem. Lett., 1953, (1994) was dissolved in 4N hydrochloric acid (4 ml), and the mixture was stirred for 20 minutes at room temperature. The reaction mixture was extracted with dichloromethane and washed with pure water. The organic layer was dried over anhydrous sodium sulfate, filtrated and concentrated to dryness under reduced pressure. The residue was separated and purified by silica gel column chromatography (dichloromethane/methanol=20/1 v/v) to give 165 mg of a monoester compound wherein one of the ester bonds was hydrolyzed (yield 50%).

This monoester compound (165 mg, 0.26 mmol) was dissolved in anhydrous tetrahydrofuran (5 ml) containing 4-dimethylaminopyridine (62.9 mg, 0.51 mmol), and the mixture was cooled to −15° C. under a nitrogen atmosphere. Chloride pivalate (63 µl, 0.51 mmol) was added, and the mixture was stirred for 30 minutes. 1-(3-Aminopropyl) imidazole (150 µl, 1.28 mmol) was added, and the mixture was reacted at −10–0° C. for 1 hour and at room temperature for 4 hours. The solvent was removed under reduced pressure, and the residue was extracted with dichloromethane, which was followed by washing with pure water. Then, the organic layer was dried over anhydrous sodium sulfate, filtrated and concentrated to dryness under reduced pressure. The residue was separated and purified by silica gel column chromatography (chloroform/methanol= 20/1 v/v) to give 100 mg of 8,13-bis(1'-methoxyethyl)-2-(2'-methyloxycarbonylethyl)-18-(2'-(3"-imidazolyl)propyl)aminocarbonylethyl)-3,7,12,17-tetramethyl-21H,23H-porphyrin (yield 52%).

Elemental analysis (% by weight): C 69.4 (69.1), H 6.98 (7.14), N 13.4 (13.1) wherein the values in the parentheses are the calculated values of $C_{43}H_{53}N_7O_5$.

Thin-layer chromatography (Merck silica gel plate, chloroform/methanol=20/1 v/v): Rf: 0.42 (monospot)

FAB-mass spectrum: 748[M]$^+$

Infrared absorption spectrum (cm$^{-1}$): 1645 ($v_{c=o}$ (amide)), 1732 ($v_{c=o}$ (ester))

Visible absorption spectrum: (chloroform) $\lambda_{max}$: 623, 568, 533, 499, 402 nm $^1$H NMR (CDCl$_3$, TMS standard), δ (ppm): 10.5, 10.0 (4H, m, meso-H), 6.9, 6.1 (3H, t, imidazole ring H), 6.0 (2H, s, (CH$_3$O)CH—), 4.3 (4H, t, —CH$_2$CH$_2$COO—), 3.8–3.6 (18H, m, CH$_3$ $_{O—,\ CH3}$—), 3.3–3.1 (6H, t, —CH$_2$CH$_2$COO—, —CONHCH$_2$—), 2.9 (2H, t, —CH$_2$Im), 2.3 (6H, s, (CH$_3$O)CHCH$_2$), 1.8 (3H, s, COOCH$_3$), 1.3 (2H, m, —CH$_2$CH$_2$CH$_2$—)

The porphyrin derivative (100 mg, 0.13 mmol) thus obtained was dissolved in dimethylformamide (10 ml). After thorough displacement with nitrogen gas, iron (II) chloride (266 mg, 1.34 mmol) was quickly added, and the mixture was reacted at 60° C. for 2 hours. The solvent was removed under reduced pressure, and the obtained solid residue was dissolved in chloroform and washed with water. The organic layer was dehydrated over anhydrous sodium sulfate. The residue was filtered and the filtrate was concentrated to dryness under reduced pressure. The obtained solid residue was separated and purified by silica gel column chromatography (chloroform/methanol=5/1 v/v) to give the objective fractions, which were dried in vacuo, whereby 84 mg of the desired porphyrin iron complex was obtained (yield 78%).

Elemental analysis (% by weight): C 61.8 (61.7), H 6.41 (6.38), N 11.4 (11.7) wherein the values in the parentheses are the calculated values of $C_{43}H_{51}N_7O_5FeCl$.

Thin-layer chromatography (Merck silica gel plate, chloroform/methanol=10/1 v/v): Rf: 0.34 (monospot)

FAB-mass spectrum: 801[M-Cl]$^+$

Infrared absorption spectrum (cm$^{-1}$): 1652 ($v_{c=o}$ (amide)), 1728 ($v_{c=o}$ (ester))

Visible absorption spectrum: (chloroform) $\lambda_{max}$: 371, 500, 535 nm

To a solution of this complex (0.14 mmol) in dimethyl sulfoxide (12 ml) was added human serum albumin (0.1 mmol) in phosphate buffer (100 ml, pH 7.4, 1/30 mM), which was followed by shaking. The mixture was concentrated to 20 ml by ultrafiltration (ultrafilter manufactured by ADVANTEC; cut off molecular weight 20,000). An aqueous solution of phosphate buffer (92 ml, pH 7.4, 1/30 mM) was added and the mixture was shaken, which was followed by concentration by ultrafiltration and dilution with an aqueous solution of phosphate buffer, whereby the desired dispersion of porphyrin iron (III) complex-albumin inclusion compound was obtained. This dispersion was preserved at room temperature or 4° C. for several months. As a result, no sedimentation or coagulation was found, and the dispersion was stable.

A small amount of an aqueous solution of sodium dithionite was added to this dispersion under nitrogen atmosphere to reduce the central metal iron of the porphyrin complex to a divalent iron, whereby the objective dispersion of 8,13-bis(1'-methoxyethyl)-2-(2'-methoxycarbonylethyl)-18-(2'-(3"-imidazolyl)propyl)aminocarbonyl-ethyl)-3,7,12,17-tetramethyl-porphyrinato iron (II) complex-albumin inclusion compound was obtained. This dispersion was diluted 1/50-fold and transferred into a quartz spectrometry cell, and the cell was sealed under a nitrogen atmosphere. The visible absorption spectra thereof were $\lambda_{max}$: 552 nm, 419 nm, which correspond to the spectrum of a penta-coordinated deoxy type complex having one intramolecular base.

The spectrum immediately changed when an oxygen gas was passed through this dispersion, giving spectra of $\lambda_{max}$: 567 nm, 536 nm, 408 nm, which apparently suggests that the porphyrin iron (II) complex included in albumin had changed to an oxygenated complex. The half life time of the above-mentioned oxygenated complex was within one hour at 25° C. A carbon monoxide gas was passed through the dispersion of the deoxy type complex, as a result of which the visible absorption spectra ($\lambda_{max}$: 560 nm, 631 nm, 412 nm) suggesting the formation of a carbon monoxide complex were obtained. This carbon monoxide complex was extremely stable at room temperature.

EXAMPLE 7

In the same manner as in Example 5 except that 8,13-bis (1'-octadecanoxyethyl)-2-(2'-octadecanoxycarbonylethyl)-18-(2'-(10"-(2"'-methyl-1"'-imidazolyl)decane) aminocarbonylethyl)-3,7,12,17-tetramethyl-porphyrinato iron (III) complex was used instead of the porphyrin iron (III) complex used in Example 1 and bovine serum albumin was used instead of human serum albumin, a dispersion of 8,13-bis(1'-octadecanoxyethyl)-2-(2'-octadecanoxycarbonylethyl)-18-(2'-(10"-(2"'-methyl-1"'-imidazolyl)decane)aminocarbonylethyl)-3,7,12,17-tetramethyl-porphyrinato iron (II) complex-albumin inclusion compound was prepared. The visible absorption spectra were $\lambda_{max}$: 553 nm, 420 nm, which correspond to the spectrum of a deoxy type complex. The aeration of oxygen gas in the same manner as in Example 1 provided visible absorption spectra ($\lambda_{max}$: 567 nm, 536 nm, 407 nm) corresponding to the spectrum of an oxygenated complex. The half life time of the oxygenated complex was within one hour at 25° C. A carbon monoxide gas was passed through the dispersion of this deoxy type complex, whereby the spectra ($\lambda_{max}$: 560 nm, 531 nm, 413 nm) suggesting the formation of a carbon monoxide complex were obtained. This carbon monoxide complex was extremely stable at room temperature.

EXPERIMENTAL EXAMPLE 1

The number of porphyrin iron complex bound to albumin in the inclusion compound of Example 1 as determined from the Scatchard plot was 1. The equilibrium constant was $2.6 \times 10^6$ ($M^{-1}$), thereby clarifying that the bond was almost as strong as in bilirubin and the like. The repetitive cycle of deoxy type complex and oxy type complex was observed more than 100 times at 25° C. The affinity for oxygen ($P_{1/2}(O_2)$) was 24 Torr (37° C.). The oxygen carrying efficiency between lung (110 Torr) and peripheral tissues (40 Torr) as estimated from the oxygen binding dissociation equilibrium curve was about 20% (37° C.), thereby suggesting the effective action of the inclusion compound of the present invention as an oxygen carrier replacing erythrocytes. The behavior of the oxygen coordinated complex in the inclusion compound of the present invention was clarified from the enthalpy/entropy changes caused by oxygen binding, and found to be about the same as hemoglobin in erythrocytes. The oxygen binding dissociation rate constant $k_{on}$ and $k_{off}$ as determined by laser flash photolysis was $2.4 \times 10^8$ ($M^{-1}s^{-1}$) and $3.2 \times 10^3$ ($s^{-1}$), respectively, thereby suggesting the ability of the inclusion compound of the present invention to bind or dissociate oxygen faster than erythrocytes. From the above results, it is clear that the inclusion compound of the present invention is capable of carrying oxygen sufficiently even when the compound is carried at high speeds in the body.

The substituted porphyrin metal complex-albumin inclusion compound of the present invention comprises a porphyrin metal complex as an oxygen adsorption/desorption site and functions as an oxygen carrier which is superior in biocompatibility, capable of adsorption and desorption of oxygen under physiological conditions, and is rather easily produced at an industrial scale.

What is claimed is:

1. A porphyrin metal complex-albumin inclusion compound comprising albumin and a substituted porphyrin metal complex wherein said substituted porphyrin metal complex comprising, as a central, coordinated metal, a transitional metal belonging to the fourth or fifth period of the periodic law, is included in the albumin wherein the substituted porphyrin metal complex is a 5,10,15,20-tetra[α,α,α,α-o-(substituted amide)phenyl]porphyrin metal complex of the following formula (I)

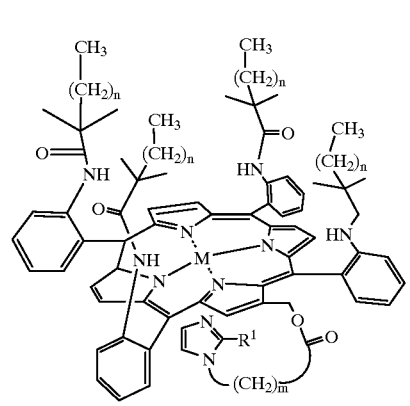

wherein $R^1$ is a hydrogen or a methyl, M is an iron or cobalt ion, n is an integer of from 0 to 17 and m is an integer of from 3 to 17 or

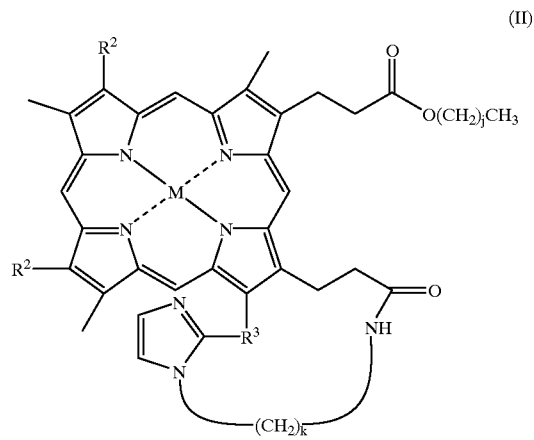

wherein the two $R^2$ groups are the same of different and each is a vinyl or a 1-alkyloxyethyl group of the formula: —(CH$_3$)CHO(CH$_2$)$_h$CH$_3$ wherein h is an integer of from 0 to 17, $R^3$ is a hydrogen or a methyl, M is an iron or cobalt ion, j is an integer of from 0 to 17 and k is an integer of from 3 to 10.

2. The porphyrin metal complex-albumin inclusion compound of claim 1, wherein the substituted porphyrin metal complex is a 5,10,15,20-tetra[α,α,α,α-o-(substituted amide) phenyl]porphyrin metal complex of the following formula (I)

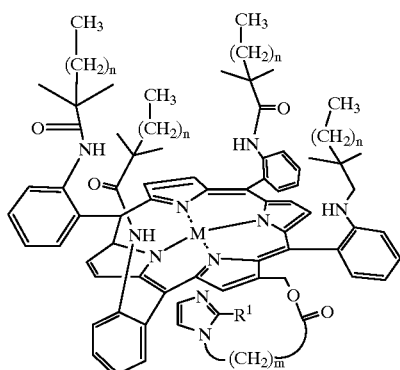

(I)

wherein R¹ is a hydrogen or a methyl, M is an iron or cobalt ion, n is an integer of from 0 to 17 and m is an integer of from 3 to 17.

3. The porphyrin metal complex-albumin inclusion compound of claim 1, wherein the substituted porphyrin metal complex is a porphyrin metal complex of the formula (II)

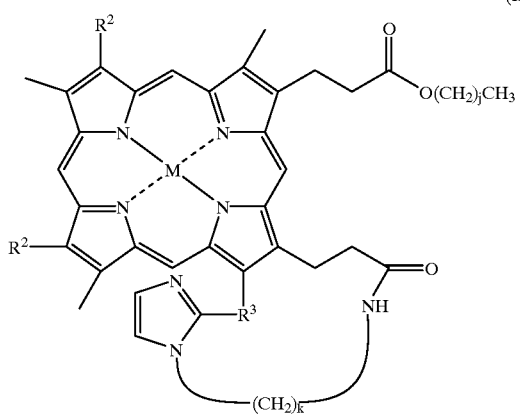

(II)

wherein the two R² groups are the same or different and each is a vinyl or a 1-alkyloxyethyl group of the formula: —(CH₃)CHO(CH₂)ₕCH₃ wherein h is an integer of from 0 to 17, R³ is a hydrogen or a methyl, M is an iron or cobalt ion, j is an integer of from 0 to 17 and k is an integer of from 3 to 10.

4. The inclusion compound of claim 2, wherein the iron or cobalt is divalent.

5. The inclusion compound of claim 3, wherein the iron or cobalt is divalent.

6. The inclusion compound of claim 1, wherein the albumin is a human serum albumin or a recombinant human serum albumin.

7. The inclusion compound of claim 2, wherein the albumin is a human serum albumin or a recombinant human serum albumin.

8. The inclusion compound of claim 1, wherein the substituted porphyrin metal complex is a 2-(8'-(2"-methyl-1"-imidazolyl)octanoyloxymethyl)-5,10,15,20-tetrakis(α,α,α,α-o-pivalamidophenyl)porphyrinato iron complex.

9. The inclusion compound of claim 1, wherein the substituted porphyrin metal complex is a 2-(18'-(N-imidazolyl)octadecanoyloxymethyl)-5,10,15,20-tetrakis(α,α,α,α-o-(2,2-dimethyloctadecanamidophenyl)porphyrinato iron complex a 2-(8'-(N-imidazolyl)octanoyloxymethyl)-5, 10,15,20-tetrakis(α,α,α,α-o-pivalamidophenyl) porphyrinato iron complex or a 2-(8'-(N-imidazolyl) octanoyloxymethyl)-5,10,15,20-tetrakis(α,α,α,α-o-(2,2-dimethylhexanamido) phenyl)porphyrinato cobalt complex.

10. An oxygen carrier composition comprising, as an active ingredient, a porphyrin metal complex-albumin inclusion compound that comprises albumin and a substituted porphyrin metal complex wherein said substituted porphyrin metal complex comprising, as a central, coordinated metal, a transitional metal belonging to the fourth or fifth period of the periodic law, is included in the albumin wherein the substituted porphyrin metal complex is a 5,10,15,20-tetra[α,α,α,α-o-(substituted amide)phenyl]porphyrin metal complex of the following formula (I)

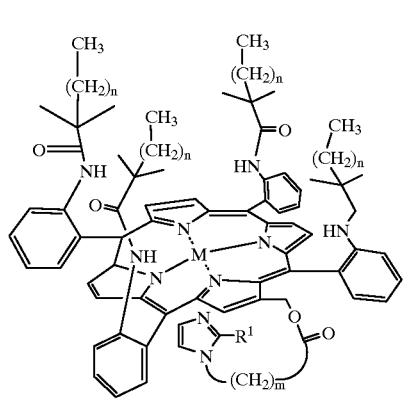

(I)

wherein R¹ is a hydrogen or a methyl, M is an iron or cobalt ion, n is an integer of from 0 to 17 and m is an integer of from 3 to 17 or

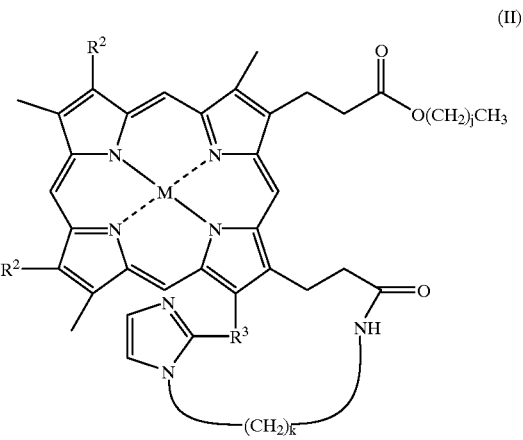

(II)

wherein the two R² groups are the same of different and each is a vinyl or a 1-alkyloxyethyl group of the formula: —(CH₃)CHO(CH₂)ₕCH₃ wherein h is an integer of from 0 to 17, R³ is a hydrogen or a methyl, M is an iron or cobalt ion, j is an integer of from 0 to 17 and k is an integer of from 3 to 10.

11. The oxygen carrier composition of claim 10, wherein the substituted porphyrin metal complex is a 5,10,15,20-tetra[α,α,α,α-o-(substituted amide)phenyl]porphyrin metal complex of the following formula (I)

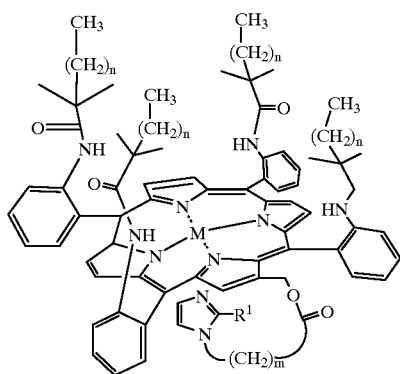

(I)

wherein $R^1$ is a hydrogen or a methyl, M is an iron or cobalt ion, n is an integer of from 0 to 17 and m is an integer of from 3 to 17.

12. The oxygen carrier composition of claim 10, wherein the substituted porphyrin metal complex is a porphyrin metal complex of the formula (II)

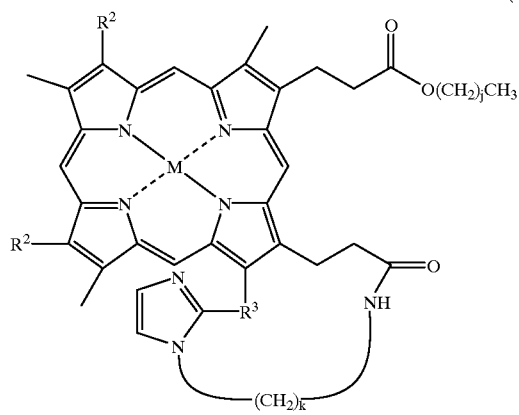

(II)

wherein the two $R^2$ groups are the same or different and each is a vinyl or a 1-alkyloxyethyl group of the formula: —(CH$_3$)CHO(CH$_2$)$_h$CH$_3$ wherein h is an integer of from 0 to 17, $R^3$ is a hydrogen or a methyl, M is an iron or cobalt ion, j is an integer of from 0 to 17 and k is an integer of from 3 to 10.

13. The oxygen carrier composition of claim 11, wherein the iron or cobalt is divalent.

14. The oxygen carrier composition of claim 12, wherein the iron or cobalt is divalent.

15. The oxygen carrier composition of claim 10, wherein the albumin is a human serum albumin or a recombinant human serum albumin.

16. The oxygen carrier composition of claim 11, wherein the albumin is a human serum albumin or a recombinant human serum albumin.

17. The oxygen carrier composition of claim 10, wherein the substituted porphyrin metal complex is a 2-(8'-(2"-methyl-1"-imidazolyl)octanoyloxymethyl)-5,10,15,20-tetrakis(α,α,α,α-o-pivalamidophenyl)porphyrinato iron complex.

18. The oxygen carrier composition of claim 10, wherein the substituted porphyrin metal complex is a 2-(18'-(N-imidazolyl)octadecanoyloxymethyl)-5,10,15,20-tetrakis(α, α,α,α-o-(2,2-dimethyloctadecanamidophenyl)porphyrinato iron complex, a 2-(8'-(N-imidazolyl)octanoyloxymethyl)-5, 10,15,20-tetrakis(α,α,α,α-o-pivalamidophenyl) porphyrinato iron complex or a 2-(8'-(N-imidazolyl) octanoyloxymethyl)-5,10,15,20-tetrakis(α,α,α,α-o-(2-,2 -dimethylhexanamido)phenyl)porphyrinato cobalt complex.

* * * * *